Dec. 28, 1954 G. MERRILL Plant Pat. 1,338

PEACH TREE

Filed April 27, 1954

WITNESS

Addison E. Avery

INVENTOR

Grant Merrill

Webster & Webster

ATTYS.

United States Patent Office

Plant Pat. 1,338

Patented Dec. 28, 1954

1,338

PEACH TREE

Grant Merrill, Red Bluff, Calif.

Application April 27, 1954, Serial No. 426,058

1 Claim. (Cl. 47—62)

This invention relates to a new and distinct variety of peach tree which bears large, yellow fleshed, highly colored, freestone fruit.

The instant variety is characterized by the following features of novelty:

As compared to the Merrill Fiesta peach (United States Plant Patent No. 1,099) which the present variety most closely resembles, the fruit has more external red color, and a ripening period approximately two weeks later.

As compared to the Merrill Rodeo peach (United States Plant Patent No. 1,097), the fruit ripens approximately one week later, has more external red color, and the variety is self-fertile, whereas the Merrill Rodeo is self-sterile.

As compared to late ripening freestone peach varieties generally, the flesh and skin of the fruit do not possess the undesirable green so commonly found in such varities, nor does the fruit have the mealiness thereof. Although the fruit is meaty, it is not mealy, and approaches mid-season quality.

In addition, the fruit is quite highly colored for a late ripening freestone peach; more nearly resembling a mid-season peach in its over-all color, as well as in its eating and other qualities.

Further, the flesh of the fruit darkens very little or not at all on exposure to air, so that the fruit is very desirable for table, culinary, canning, freezing, or shipping use.

The present variety of peach tree was originated by me in my experimental orchard near Red Bluff, California, as follows:

Seeds from fruit, purchased on the open market, of the Kirkman Gem peach (United States Plant Patent 506) were planted, and the resulting seedlings were permitted to grow to maturity. These seedlings were very carefully observed by me with respect to their fruit and tree characteristics; the present variety having been selected by me from said seedlings as being of especial promise for commercial planting, by reason of the advantageous late ripening period and the excellent fruit quality.

Subsequent to its origination and selection, I asexually reproduced the variety by grafting onto mature orchard trees of the Golden Jubilee peach (unpatented) on my ranch near Red Bluff, California, and these grafts—when they came into bearing—were found to run true to the parent in all respects.

Figures 1, 2:
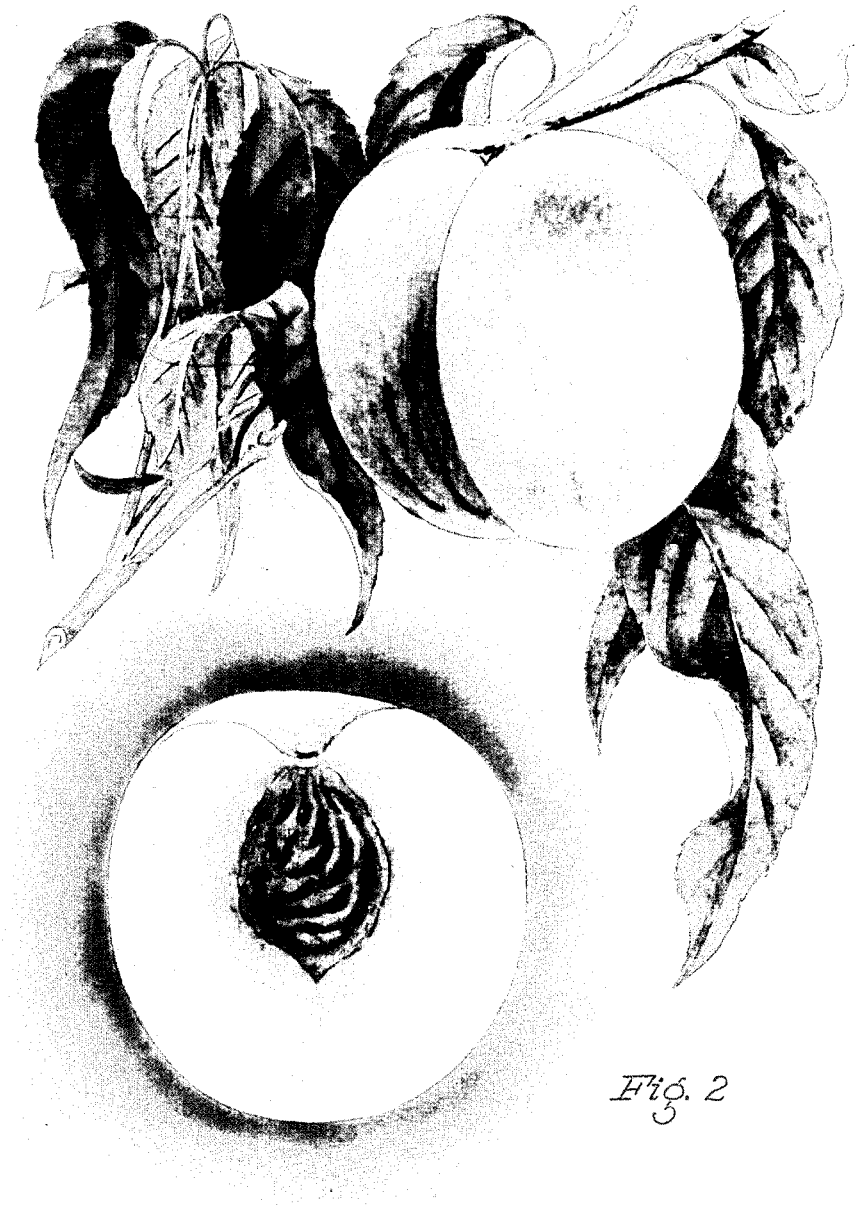
Fig. 1 is an elevation of the fruit of the present variety, together with leaves and twigs.
Fig. 2 is a cross section of one of the fruit, with the stone exposed but remaining in place.

Referring now more specifically to the pomological details of this new and distinct variety of peach tree, the following is an outline description thereof; all major color plate identifications being by reference to Maerz and Paul Dictionary of Color:

Tree: Medium size; medium vigorous; medium spreading. Density or openness—controlled by pruning. Form—controlled by pruning. Productive; regular bearer.

Trunk: Medium stocky; medium shaggy.

Branches: Medium stocky; medium shaggy.
- *Color.*—Brown gray.
- *Lenticels.*—Numerous; medium—small.

Leaves:
- *Size.*—Medium; average length—6½"; average width—1 9/16". Medium thickness.
- *Form.*—Lanceolate; apex acuminate.

- *Texture.*—Smooth to slightly rugose along midrif.
- *Margin.*—Coarsely serrate.
- *Petiole.*—Short medium slender.
- *Glands.*—Average 1 to 5, mostly 3. Alternate; small. Position, along on petiole and lower edge of leaf. Reniform.
- *Color.*—Top side—medium green (23–L–2). Under side—Lighter Green (22–K–3).

Flower buds: Medium size; medium short; plump; free; pubescent.

Flowers: Dates of first and last bloom—March 4, 1954, and March 16, 1954. Medium season; medium size; light pink; pollen fertile. Anthers yellow to orange.

Fruit:
- *Maturity when described on October 3, 1953.*—Ripe (firm ripe).
- *Date of first picking.*—October 3, 1953.
- *Date of last picking.*—October 20, 1953.
- *Size.*—Uniform; large. Average axial diameter—3"; average transverse in suture plane—3 3/16".
- *Form.*—Uniform; slightly unsymmetrical; globose.
- *Suture.*—Distinct and extends from base to beyond but discontinues at apex, with slight depression beyond pistil point. Medium depth.
- *Ventral surface.*—Slightly rounded. Lipped toward base on both sides. Lips equal.
- *Cavity.*—Rounded. Elongated in suture plane, with suture showing on both sides. Average depth—⅜"; average breadth—1⅛". No markings.
- *Base.*—Truncate.
- *Apex.*—Rounded to truncate; pistil point apical.

Skin: Thick; tough; tenacious to flesh.
- *Tendency to crack.*—None.
- *Down.*—Moderate; medium; rolls up when rubbed.
- *Color.*—Yellow (10–K–7), with over half of the surface mottled red (4–K–10 shading to 4–L–10), with dark red stripes (7–L–6).

Flesh:
- *Surface of pit cavity.*—Pink.
- *Amygdalin.*—Moderate.
- *Juice.*—Moderate.
- *Texture.*—Firm and meaty.
- *Fibers.*—Moderate; coarse.
- *Ripens.*—Evenly.
- *Flavor.*—Mild; subacid.
- *Aroma.*—Moderate.
- *Darkening on exposure to air.*—Very little or no discoloration on exposure to the air.
- *Color.*—Yellow (9–J–4), shading darker (9–L–7) toward the outside, mottled red (4–J–6 shading to 4–K–7) next to stone, especially on the sunny side.

Stone: Free.
- *Fibers.*—Short.
- *Size.*—Medium. Average length—1⅝"; average breadth—1⅛"; average thickness—⅞".
- *Form.*—Obovate.
- *Base.*—Oblique.
- *Hilum.*—Oblong.
- *Apex.*—Cuspidate.
- *Surface.*—Irregularly furrowed near base; pitted from base to above center.
- *Ridges.*—Rounded.
- *Pits.*—Elongated.
- *Ventral edge.*—Medium, with wing throughout.
- *Dorsal edge.*—Full; shallow.
- *Ridges.*—On either side.
- *Tendency to split.*—None.
- *Color.*—Deep brown (7–L–12 shading to 8–L–6).

Use: Market; local market; long distance shipping; culinary; canning; freezing.

Eating quality: Best in comparision to other late ripening freestone peaches.

Keeping quality: Excellent.

Shipping quality: Excellent.

The tree and its fruit herein described may vary in slight detail due to climatic and soil conditions under which the variety may be grown.

Having thus described my invention I claim:

A new and distinct variety of peach tree, as illustrated and described, which bears large, uniform, globose freestone fruit; characterized—in comparison to the Merrill Fiesta peach—by fruit which ripens two weeks later, and has more external red color; characterized— in comparison to the Merrill Rodeo peach by self-fertility and by fruit which ripens one week later, and has more external red color; and further characterized by fruit having high external color and without the green of flesh and skin common to other late ripening varieties of freestone peach, by flesh which is firm, meaty, and darkens very little or none at all on exposure to air, and by excellent eating, keep and shipping qualities.

No references cited.